US012667644B2

(12) United States Patent
Aied et al.

(10) Patent No.: US 12,667,644 B2
(45) Date of Patent: Jun. 30, 2026

(54) IODINE-INFUSED ULTRA HIGH MOLECULAR WEIGHT POLYETHYLENE

(71) Applicant: Biomet Manufacturing, LLC, Warsaw, IN (US)

(72) Inventors: Ahmed Aied, London (GB); Mohammed Imran Khan, Berkshire (GB); Gil Machado, Redfield (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 743 days.

(21) Appl. No.: 17/634,509

(22) PCT Filed: Aug. 11, 2020

(86) PCT No.: PCT/US2020/045770
§ 371 (c)(1),
(2) Date: Feb. 10, 2022

(87) PCT Pub. No.: WO2021/030350
PCT Pub. Date: Feb. 18, 2021

(65) Prior Publication Data
US 2022/0280688 A1 Sep. 8, 2022

Related U.S. Application Data

(60) Provisional application No. 62/885,530, filed on Aug. 12, 2019.

(51) Int. Cl.
*A61L 27/16* (2006.01)
*A61L 27/54* (2006.01)
(Continued)

(52) U.S. Cl.
CPC ............... *A61L 27/16* (2013.01); *A61L 27/54* (2013.01); *C08K 3/02* (2013.01); *C08K 5/13* (2013.01);
(Continued)

(58) Field of Classification Search
CPC .... A61L 27/16; A61L 27/54; A61L 2300/106; A61L 2300/202; A61L 2300/404; A61L 2430/24; C08K 3/02; C08K 5/13
(Continued)

(56) References Cited

U.S. PATENT DOCUMENTS

2003/0018306 A1 1/2003 Bucay-Couto et al.
2008/0058869 A1 * 3/2008 Stopek ............ A61B 17/06066 606/228
(Continued)

FOREIGN PATENT DOCUMENTS

AU 2020329917 B2 1/2024
CN 1115254 A 1/1996
(Continued)

OTHER PUBLICATIONS

"Chinese Application Serial No. 202080070857.4, Office Action mailed Jul. 5, 2022", w/ English translation, 23 pgs.
(Continued)

*Primary Examiner* — David T Karst
(74) *Attorney, Agent, or Firm* — SCHWEGMAN LUNDBERG & WORSSNER, P.A.

(57) ABSTRACT

Various embodiments disclosed relate to an implant including a crosslinked iodine-infused polyethylene. In various embodiments, the implant can be made by exposing the polyethylene to a source of iodine such that the polyethylene is infused with iodine. In various embodiments, a method of preventing microbe formation on or around an implant includes implanting a crosslinked iodine-infused implant comprising polyethylene, wherein iodine is released gradually from the implant after the implantation.

7 Claims, 6 Drawing Sheets

(51) Int. Cl.
*C08K 3/02* (2006.01)
*C08K 5/13* (2006.01)

(52) U.S. Cl.
CPC ... *A61L 2300/106* (2013.01); *A61L 2300/202* (2013.01); *A61L 2300/404* (2013.01); *A61L 2430/24* (2013.01)

(58) Field of Classification Search
USPC .......................................................... 523/115
See application file for complete search history.

(56) References Cited

U.S. PATENT DOCUMENTS

| | | | | |
|---|---|---|---|---|
| 2008/0090934 | A1 | 4/2008 | Muratoglu et al. | |
| 2014/0051771 | A1* | 2/2014 | Hufen | A61N 1/05 525/227 |
| 2014/0183794 | A1 | 7/2014 | Muratoglu et al. | |
| 2015/0322239 | A1 | 11/2015 | He et al. | |
| 2015/0376349 | A1 | 12/2015 | He et al. | |

FOREIGN PATENT DOCUMENTS

| | | | | |
|---|---|---|---|---|
| CN | 1142193 | A | 2/1997 | |
| CN | 101243984 | A | 8/2008 | |
| CN | 101687942 | A | 3/2010 | |
| CN | 102580141 | A | 7/2012 | |
| CN | 104208744 | A | 12/2014 | |
| CN | 107207741 | A | 9/2017 | |
| CN | 109440211 | A | 3/2019 | |
| CN | 114502208 | A | 5/2022 | |
| EP | 1369135 | A1 | 12/2003 | |
| EP | 1750614 | A1 | 2/2007 | |
| EP | 1813293 | A2 | 8/2007 | |
| JP | 2002518351 | A | 6/2002 | |
| JP | 2005504659 | A | 2/2005 | |
| JP | 2007536998 | A | 12/2007 | |
| JP | 2011527353 | A | 10/2011 | |
| JP | 2022544657 | A | 10/2022 | |
| JP | 7440615 | B2 | 2/2024 | |
| JP | 2024045562 | A | 4/2024 | |
| WO | WO-9620019 | A1 | 7/1996 | |
| WO | WO-0074743 | A1 | 12/2000 | |
| WO | WO-2013164016 | A1 | 11/2013 | |
| WO | WO-2016139593 | A1 | 9/2016 | |
| WO | WO-2018119493 | A1 * | 7/2018 | A61L 27/16 |
| WO | WO-2021030350 | A1 | 2/2021 | |

OTHER PUBLICATIONS

"European Application Serial No. 20764190.3, Response to Communication pursuant to Rules 161(1) and 162 EPC filed Oct. 4, 2022", 14 pgs.
"International Application Serial No. PCT/US2020/045770, International Preliminary Report on Patentability mailed Feb. 24, 2022", 9 pgs.
Hnatowicz, V, "Redistribution of iodine in polyethylene modified by ion irradiation", Czechoslovak Journal of Physics ?47?, (Feb. 28, 1997), 255-258.
"International Application Serial No. PCT/US2020/045770, International Search Report mailed Nov. 6, 2020", 5 pgs.
"International Application Serial No. PCT/US2020/045770, Written Opinion mailed Nov. 6, 2020", 7 pgs.
Shirai, T, et al., "Antibacterial Iodine-Supported Titanium Implants", Acta Biomaterialia, Elsevier, Amsterdam, NL, vol. 7, No. 4, (Nov. 23, 2010), 1928-1933.
"Australian Application Serial No. 2020329917, First Examination Report mailed Jan. 6, 2023", 3 pgs.
"Australian Application Serial No. 2020329917, Response filed Mar. 31, 2023 to First Examination Report mailed Jan. 6, 2023", 15 pgs.
"Australian Application Serial No. 2020329917, Response filed Aug. 10, 2023 Subsequent Examiners Report mailed Apr. 24, 2023", 18 pgs.
"Australian Application Serial No. 2020329917, Subsequent Examiners Report mailed Apr. 24, 2023", 3 pgs.
"Australian Application Serial No. 2023285973, First Examination Report mailed Jun. 3, 2025", 3 pgs.
"Australian Application Serial No. 2023285973, Voluntary Amendment Filed Feb. 14, 2024", 13 pgs.
"Canadian Application Serial No. 3,150,685, Examiners Rule 86(2) Requisition mailed Feb. 27, 2024", 3 pgs.
"Canadian Application Serial No. 3,150,685, Office Action mailed Feb. 13, 2023", 4 pgs.
"Canadian Application Serial No. 3,150,685, Response filed Jun. 5, 2023 to Office Action mailed Feb. 13, 2023", 15 pgs.
"Canadian Application Serial No. 3,150,685, Response filed Jun. 25, 2024 to Examiners Rule 86(2) Requisition mailed Feb. 27, 2024", 7 pgs.
"Chinese Application Serial No. 202080070857.4, Decision of Rejection mailed Sep. 7, 2023", W/English Translation, 20 pgs.
"Chinese Application Serial No. 202080070857.4, Office Action mailed Jan. 20, 2023", w/ English Translation, 16 pgs.
"Chinese Application Serial No. 202080070857.4, Office Action mailed Apr. 13, 2023", w/ English Translation, 20 pgs.
"Chinese Application Serial No. 202080070857.4, Response filed Apr. 4, 2023 to Office Action mailed Jan. 20, 2023", w/ English claims, 9 pgs.
"Chinese Application Serial No. 202080070857.4, Response filed Nov. 21, 2022 to Office Action mailed Jul. 5, 2022", w/ English translation, 9 pgs.
"Chinese Application Serial No. 202080070857.4, Response Filed Dec. 22, 2023 to Decision of Rejection mailed Sep. 7, 2023", W/ English Claims, 10 pgs.
"European Application Serial No. 20764190.3, Communication Pursuant to Article 94(3) EPC mailed Jul. 15, 2025", 8 pgs.
"European Application Serial No. 20764190.3, Communication Pursuant to Article 94(3) EPC mailed Jul. 19, 2023", 7 pgs.
"European Application Serial No. 20764190.3, Response filed Nov. 15, 2023 to Communication Pursuant to Article 94(3) EPC mailed Jul. 19, 2023", 10 pgs.
"Japanese Application Serial No. 2022-508857, Final Notification of Reasons for Rejection mailed Aug. 15, 2023", W/English Translation, 7 pgs.
"Japanese Application Serial No. 2022-508857, Notification of Reasons for Rejection mailed Mar. 28, 2023", W/English Translation, 8 pgs.
"Japanese Application Serial No. 2022-508857, Response filed Jun. 28, 2023 to Notification of Reasons for Rejection mailed Mar. 28, 2023", w/ English claims, 10 pgs.
"Japanese Application Serial No. 2022-508857, Response Filed Nov. 15, 2023 to Final Notification of Reasons for Rejection mailed Aug. 15, 2023", w/ English Claims, 6 pgs.
"Japanese Application Serial No. 2024-021363, Notification of Reasons for Refusal mailed Apr. 22, 2025", w/ English translation, 7 pgs.
"Japanese Application Serial No. 2024-021363, Notification of Reasons for Refusal mailed Apr. 22, 2025", w/ English Claims, 6 pgs.

* cited by examiner

IODINE-INFUSED ULTRA HIGH MOLECULAR WEIGHT POLYETHYLENE

CLAIM OF PRIORITY

This application is a U.S. National Stage Application under 35 U.S.C. 371 from International Application Serial No. PCT/US2020/045770, filed on Aug. 11, 2020, published as WO 2021/030350 A1 on Feb. 18, 2021, which claims the benefit of U.S. Provisional Patent Application Ser. No. 62/885,530, filed on Aug. 12, 2019, the benefit of priority of each of which is claimed hereby, and each of which is incorporated by reference herein in its entirety.

BACKGROUND OF THE INVENTION

Ultra high molecular weight polyethylene (UHMWPE) is the most widely used material for orthopedic implants that articulate, such as for hip, knee, ankle, elbow and shoulder joint replacement due to osteoarthritis. In particular, highly crosslinked UHMWPE is often used, which is crosslinked by the use of high energy irradiation such as gamma or electron beam. Crosslinking reduces the wear rate of UHMWPE significantly, reducing polyethylene particulate burden, which can lead to osteolysis. In some implants, antioxidants are added to highly crosslinked UHMWPE to combat free radical burden.

In UHMWPE implants, infection is one of the leading causes of revision of joint replacements. As antibiotic resistance of bacteria increases, infection has become more difficult to deal with in the context of joint replacements.

SUMMARY OF THE INVENTION

In various embodiments, the present invention provides an implant including an iodine-infused polyethylene.

In various embodiments, the present invention provides a method of making an implant by exposing the polyethylene to a source of iodine such that the polyethylene is infused with iodine.

In various embodiments, the present invention provides a method of preventing microbe formation on or around an implant including implanting a crosslinked iodine-infused implant comprising polyethylene, wherein iodine is released gradually from the implant after the implantation.

In some embodiments, a crosslinked iodine-infused polyethylene implant can reduce bacteria formation on and near the implant due to antimicrobial efficacy of iodine.

In some embodiments, iodine-infused directly into polyethylene implants is not subject to articulation, in contrast to other antimicrobial agents such as surface coatings.

In some embodiments, infused iodine can release from the polyethylene by diffusion over time to destroy microbes on and near the implant.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
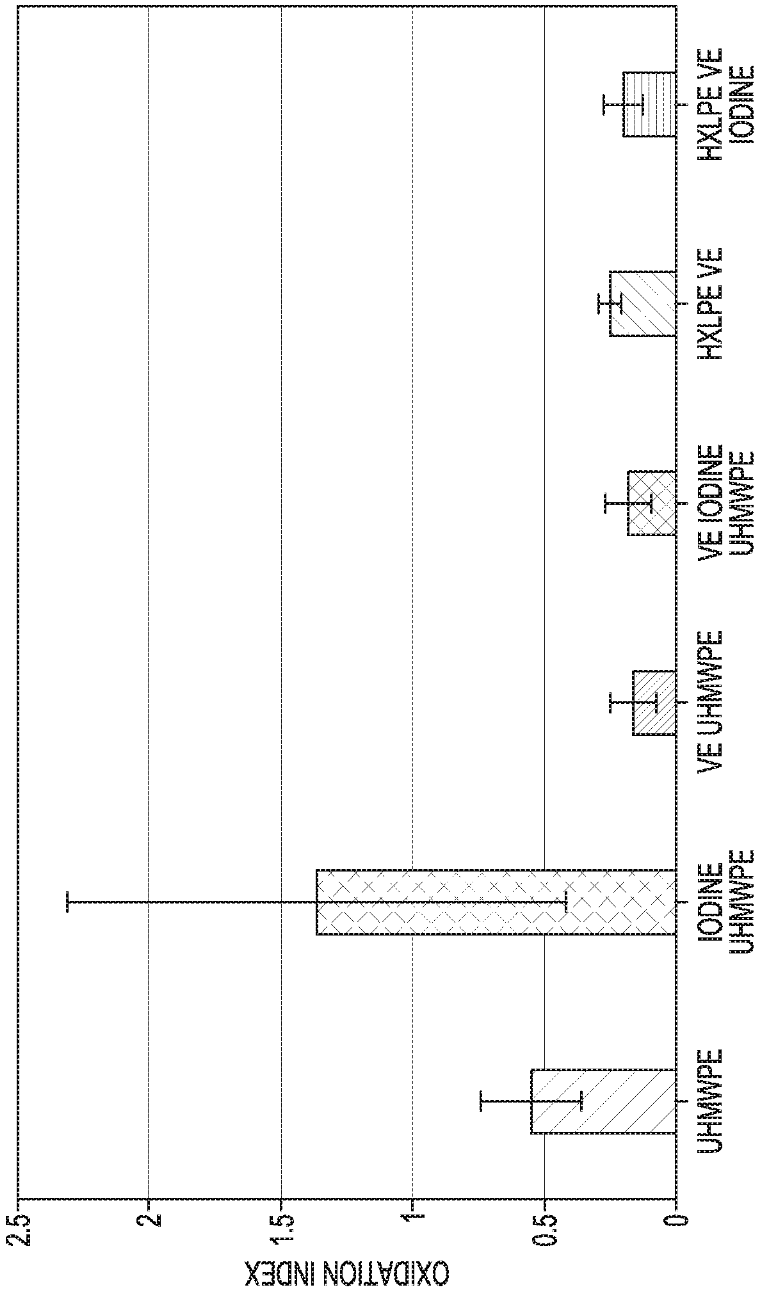
FIG. 1 is a chart depicting the oxidation index of samples in Example 3, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid; carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted ($C_1$-$C_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group, Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R$_2$, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)A, C)=HN)N(R)$_2$, C(O)N(OR)R, and C(=NOR)R, wherein R can be hydrogen or a carbon-based moiety; for example, R can be hydrogen, ($C_1$-$C_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "solvent" as used herein refers to a liquid that can dissolve a solid, liquid, or gas. Nonlimiting examples of solvents are silicones, organic compounds, water, alcohols, ionic liquids, and supercritical fluids.

The term "air" as used herein refers to a mixture of gases with a composition approximately identical to the native composition of gases taken from the atmosphere, generally at ground level. In some examples, air is taken from the ambient surroundings. Air has a composition that includes approximately 78% nitrogen, 21% oxygen, 1% argon, and 0.04% carbon dioxide, as well as small amounts of other gases.

The term "room temperature" as used herein refers to a temperature of about 15° C. to 28° C.

The term "coating" as used herein refers to a continuous or discontinuous layer of material on the coated surface, wherein the layer of material can penetrate the surface and can fill areas such as pores, wherein the layer of material can have any three-dimensional shape, including a flat or curved plane. In one example, a coating can be formed on one or more surfaces, any of which may be porous or nonporous, by immersion in a bath of coating material.

The term "surface" as used herein refers to a boundary or side of an object, wherein the boundary or side can have any perimeter shape and can have any three-dimensional shape, including flat, curved, or angular, wherein the boundary or side can be continuous or discontinuous. While the term "surface" generally refers to the outermost boundary of an object with no implied depth, when the term "pores" is used in reference to a surface, it refers to both the surface opening and the depth to which the pores extend beneath the surface into the substrate.

Overview

Microbes are commonly found on and near joint implants. Revisions of joint replacements is often done due to infection. However, microbes do not currently have resistance to iodine, as compared to, for example, anti-biotics. Iodine has a history in medicine as an antiseptic and is already present in the human body for thyroid function.

Iodine has a high antimicrobial efficacy. Infusing polymer implants, such as polyethylene implants, with iodine can allow for diffusion of that iodine over time within the human body, combating microbe build-up, biofilm formation and infection. The iodine can, for example, release into the joint space where the polyethylene implant is present to destroy infection-causing microbes. Thus, an iodine-infused polyethylene implant can be used prophylactically and to treat infections.

In various embodiments, disclosed herein is an iodine-infused polyethylene implant and method of making. The implant can be, for example, an ultra-high molecular weight polyethylene (UHMWPE) or a highly crosslinked polyethylene (HXPE) infused through a diffusion mechanism with an iodine solution, such as an iodophor (e.g. povidone-iodine), or other aqueous iodine solutions, such as solvent containing solutions. In an example, Lugol's solution can be used.

After infusion, the iodine can be held in the amorphous regions of the polyethylene implant. Once the implant is in the body, the iodine can diffuse in vivo out of the polyethylene and into the areas surrounding the implant. This can allow for antimicrobial protection by destroying microbes in the joint space and implant. Iodine can, for example, act in an anti-microbial fashion by attacking proteins in microbes.

Iodine-Infused Polyethylene Implant

In various embodiments, an implant can include an uncrosslinked, or crosslinked, iodine-infused polyethylene. The iodine can have, for example, a concentration of about 5 to about 3000 μg/cm$^3$ (e.g., about 200 to about 1000 μg/cm$^3$) in polyethylene. In some embodiments, the iodine is homogeneously distributed throughout the polyethylene. In some embodiments, the polyethylene is saturated with the iodine. In some embodiments portions of the polyethylene are selectively treated with iodine, while other portions are not treated with the iodine.

The polyethylene implant material can be, for example, ultra high molecular weight polyethylene (UHMWPE), ultra low molecular weight polyethylene, high density polyethylene, high molecular weight polyethylene, high density crosslinked polyethylene, medium density polyethylene, low density polyethylene, linear low density polyethylene, very low density polyethylene, branched polyethylene, or combinations thereof.

For example, UHMWPE is a unique form of polyethylene of extremely high molecular weight, where the molecular weight of commercial grade materials are typically in the range of 2 to 7 million. The molecular weight of commodity polyethylene is typically in the range of 50,000 to 100,000, a factor of 25 or more times lower. UHMWPE is the most widely used material for orthopedic implants that articulate, such as for hip, knee, ankle, elbow and shoulder joint replacement due to osteoarthritis.

The implant material can include UHMWPE. Any suitable proportion of the implant material can be the UHMWPE, such as about 1 wt. % to about 100 wt. % of the implant material, about 90 wt. % to about 100 wt. %, or about 1 wt. % or less, or less than, equal to, or greater than about 2, 3, 4, 5, 10, 15, 20, 25, 30, 35, 40, 45, 50, 55, 60, 65, 70, 75, 80, 85, 90, 95, 96, 97, 98, 99, or about 99.9 wt. % or more. The UHMWPE can form a homogeneous or heterogeneous mixture with other components in the implant material.

The implant material can have any suitable amount of void space therein, wherein the void space is the parts of the implant material occupied by porous regions (e.g., not occupied by a solid or liquid). The implant material can have about 0.001 vol. % to about 80 vol. % void space, about 1 vol. % to 50 vol. % void space, about 1 vol. % to about 20 vol. % void space, about 5 vol. % to about 15 vol. % void space, or about 0.001 vol. % or less, or about 0.005 vol. % void space, 0.01, 0.05, 0.1, 0.5, 1, 2, 3, 4, 5, 6, 7, 8, 9, 10, 12, 14, 16, 18, 20, 25, 30, 35, 40, 45, or about 50 vol. % void space or more. The void space in the implant material can have any suitable distribution in the implant material. In some embodiments, the void space in the implant material can be substantially homogenously distributed.

UHWMPE is a semi crystalline, linear homopolymer of ethylene, which in some embodiments can be produced by stereospecific polymerization with a Ziegler-Natta catalyst at low pressure (6-8 bar) and low temperature (66-80° C.). The synthesis of UHMWPE can result in a fine granular powder. The molecular weight and its distribution can be controlled by process parameters such as temperature, time and pressure. UHMWPE generally has a molecular weight of at least about 2,000,000 g/mol. Suitable UHMWPE materials for use as raw materials may be in the form of a powder or mixture of powders. Examples of suitable UHMWPE materials include GUR® 1020 and GUR® 1050 available from Ticona Engineering Polymers.

In addition to UHMWPE, the implant material can include any other suitable component. In certain embodiments, the UHWMPE can be combined with another crosslinkable polymer. The crosslinkable polymer can be any polymer that is crosslinkable using radiation, a chemical crosslinking agent or that can be physically cross-linked under suitable conditions. In some examples, the polymer can be a thermoplastic polymer such as, for example, an acrylonitrile butadiene styrene (ABS) polymer, an acrylic polymer, a celluloid polymer, a cellulose acetate polymer, a cycloolefin copolymer (COC), an ethylene-vinyl acetate (EVA) polymer, an ethylene vinyl alcohol (EVOH) polymer, a fluoroplastic, an ionomer, an acrylic/PVC alloy, a liquid crystal polymer (LCP), a polyacetal polymer (POM or acetal), a polyacrylate polymer, a polyacrylonitrile polymer (PAN or acrylonitrile), a polyamide polymer (PA or nylon), a polyamide-imide polymer (PAD, a polyaryletherketone polymer (PAEK or ketone), a polybutadiene polymer (PBD), a polybutylene polymer (PB), a polybutylene terephthalate polymer (PBT), a polycaprolactone polymer (PCL), a polychlorotrifluoroethylene polymer (PCTFE), a polyethylene terephthalate polymer (PET), a polycyclohexylene dimethylene terephthalate polymer (PCT), a polycarbonate polymer, a polyhydroxyalkanoate polymer (PHA), a polyketone polymer (PK), a polyester polymer, a polyethylene polymer (PE), a polyetheretherketone polymer (PEEK), a polyetherketoneketone polymer (PEKK), a polyetherimide polymer (PEI), a polyethersulfone polymer (PES), a polyethylenechlorinate polymer (PEC), a polyimide polymer (PI), a polylactic acid polymer (PLA), a polymethylpentene polymer (PMP), a polyphenylene oxide polymer (PPG), a polyphenylene sulfide polymer (PPS), a polyphthalamide polymer (PPA), a polypropylene polymer, a polystyrene polymer (PS), a polysulfone polymer (PSU), a polytrimethylene terephthalate polymer (PTT), a polyurethane polymer (PU), a polyvinyl acetate polymer (PVA), a polyvinyl chloride polymer (PVC), a polyvinylidene chloride polymer (PVDC), and a styrene-acrylonitrile polymer (SAN), Illustrative types of polyethylene in addition to the UHMWPE include, for example, ultra low molecular weight polyethylene (ULMWPE), high molecular weight polyethylene (HMWPE), high density polyethylene (HDPE), high density cross-linked polyethylene (HDXLPE), cross-linked polyethylene (PEX or XLPE), medium density polyethylene (MDPE), low density polyethylene (LDPE), linear low density polyethylene (LLDPE) and very low density polyethylene (VLDPE).

In some examples, the implant material can include a polypropylene. A polypropylene may be particularly desirable where the final product is a mesh, stent, breast implant material, suture material or other medical device. In one alternative, a polypropylene (or other polymer) may be used as one layer in a multi-layered medical device. Illustrative polypropylenes can include a homopolymeric polypropylene, a block copolymeric polypropylene, and a random copolymeric polypropylene.

In some embodiments, the implant material can include one or more suitable additives that impart a desired physical or chemical property. Illustrative suitable additives include radiopaque materials, antimicrobial materials such as silver ions, antibiotics, and microparticles and/or nanoparticles serving various functions. Preservatives, colorants and other conventional additives may also be used.

In various embodiments, the iodine-infused polyethylene implant can include an antioxidant. The antioxidant can be, for example about 0.01 wt. % to about 5.0 wt. % of the polyethylene implant (e.g., about 0.05 wt. % to about 0.50 wt. % of the polyethylene implant). In some embodiments, the antioxidant can be homogenously distributed in the polyethylene.

The iodine-infused polyethylene implant can retain mechanical strength and associated properties despite the infusion of iodine. For example, under pin-on-plate wear analysis, the polyethylene can have a mean cumulative mass loss from about 0.001 g to about 0.005 g over about 10,000 cycles to about 1,300,000 cycles of wear analysis (e.g., about 0.001 g to about 0.003 g over about 20,000 cycles to about 1,200,000 cycles of wear analysis).

Similarly, the iodine-infused polyethylene implant can retain an elastic modulus of about 250 MPa to about 400 MPa (e.g., about 300 MPa to about 350 MPa), and an elongation of break of about 475% of about 515%.

In some embodiments, the medical implant can be an orthopedic implant. In various embodiments, the medical implant can form or be part of an artificial hip, hip liner, knee, knee liner, disk replacement, shoulder, elbow, foot, ankle, finger, mandible, or bearings in an artificial heart.

Consolidation of Implant

Disclosed herein, in various embodiments, is a method of infusing a polyethylene implant with iodine. The method can include exposing the polyethylene to a source of iodine, such as an iodine solution, so that the polyethylene is infused with iodine. The solution can include, for example, an iodine solution, such as an iodophor (e.g. povidone-iodine), or other aqueous iodine solutions, such as solvent containing solutions. In an example, Lugol's solution can be used. The polyethylene can be, for example, in a resin form, a partially consolidated form, or a fully consolidated form.

Prior to infusion, the polyethylene implant can be prepared and consolidated. Prior to consolidation, the polyethylene can be mixed with various materials. For example, in some embodiments, the implant material (such as, for example, including UHMWPE) can be prepared by a method including blending the polyethylene powder with other suitable materials, such as a blend with another polymer or a blend with an antioxidant. Such processes can include physical mixing, mixing with the aid of a solvent, mixing with the aid of a solvent (e.g., $CO_2$) under supercritical temperature and pressure conditions, and ultrasonic mixing.

Consolidation can be performed after blending or preparing the material. Consolidation shapes and forms the material for the implant, determining implant material shape, size, density, mechanical properties and other attributes. Consolidation can include, for example, cold-sintering, melt-consolidation, or combinations thereof, in addition to other consolidation techniques as known in the art. Cold-sintering is a method not using melting, while melt-consolidation includes melting the polyethylene material to form it.

In some embodiments, a polyethylene powder can be cold-sintered to provide the implant material. In this case, the implant material can be substantially free of melting. The implant material can be, for example, a solid formed prior to a consolidation step including melting. For example, the implant material can be a solid formed from UHMWPE powder wherein substantially no melting occurs during formation of the implant material.

In some embodiments, the implant material can be a cold sintered material. The method can include cold-sintering polyethylene powder, and any optional additional ingredients, to form the implant material. The cold-sintering includes application of sufficient pressure under low-shear conditions to fuse the boundaries of the generally spherical powdered polyethylene particles together. The cold-sintering can include any suitable sub-melting point consolidation technique such as compression molding, direct compression molding, ram extrusion, hot isostatic pressing, ram extrusion, high pressure crystallization, injection molding, and a combination thereof.

The cold-sintering does not melt the polyethylene. The cold-sintering can generate any suitable maximum temperature in the polyethylene, such as about 30° C., 35, 40, 45, 50, 55, 60, 65, 70, 75, 80, 85, 90, 95, 100, 105, 110, 115, 120, 125, 130, 135, 140, 145, or about 150° C., so long as substantially no melting of the polyethylene occurs.

If the cold-sintering can be conducted in air, the initial compression of the polyethylene powder can reduce the air content, and more importantly oxygen content, which can reduce oxidation of polyethylene during the consolidation and during later parts of the method. In some embodiments, the cold-sintering can be conducted under near inert conditions where the air is displaced by a non-reactive gas such as nitrogen or argon, or under vacuum reduced pressure.

In some embodiments, the implant material can be melt-consolidated. The melt-consolidating can include any suitable melt consolidation procedure. The melt-consolidation can include any suitable above-melting point consolidation technique such as compression molding, direct compression molding, ram extrusion, hot isostatic pressing, ram extrusion, high pressure crystallization, injection molding, and a combination thereof. Melt-consolidating can include any suitable pressure, such as about 20 psi to 250,000 psi, about 100 psi to about 100,000 psi, about 2,000 to about 10,000 psi, or about 100 psi or less, or about 200 psi, 300, 500, 750, 1,000, 1,500, 2,000, 2,500, 5,000, 7,500, 10,000, 15,000, 20,000, 25,000, 50,000, 75,000, 100,000, 150,000, 200,000, or about 250,000 psi or more.

The melt-consolidating generates sufficient heat to melt the polyethylene. For example, the melt-consolidating can generate a minimum temperature in the polyethylene of about 60° C., 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 250, 275, or about 300° C. or more, so long as the polyethylene melts.

The melt-consolidating can be carried out in air or can be conducted under near inert conditions where the air is displaced by a non-reactive gas such as nitrogen or argon, or under vacuum reduced pressure.

Additives

In various embodiments, the present invention provides a method of adding one or more antioxidants, such as Vitamin E, to polyethylene prior to infusion with iodine. Suitable antioxidants are described in detail above.

An antioxidant can be useful in the implant as oxidation of polyethylene can occur through a free radical pathway, as shown in the following sequence:

| | |
|---|---|
| RH + IN → R• | Initiation |
| R• + $O_2$ → ROO• | |
| ROO• + RH → ROOH + R• | Propagation |
| ROOH → RO• + HO• | |
| RO• + RH → ROH + R• | Chain Branching |
| HO• + RH → HOH + R• | |
| ROO• (RO•etc.) → Inert Products | Termination |
| ROO• + AH → ROOH + A• | |
| RO• + AH → ROH + A• | Inhibition (stabilization) |
| HO• + AH → HOH + A• | |

wherein

In the above sequence, RH is the polymer (e.g., polyethylene, such as UHMWPE), IN is the initiator (e.g., irradiation), and AH is the inhibitor (e.g., free-radical scavenging antioxidant).

The antioxidant can be, for example, at least one of a tocopherol, a tocopherol phosphite, a tocotrienol, vitamin E, vitamin E acetate, vitamin E phosphite, rosemary oil, pentaerythritol tetrakis(3-(3,5-di-test-butyl-4-hydroxyphenyl) propionate), butanedioic acid dimethyl ester/4-hydroxy-2,2,6,6-tetramethyl-1-piperidine ethanol copolymer, tannic acid, bilberry extract, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol, rosmarinic acid, rutin, 5-aminosalicylic acid, butylated hydroxy anisole, butylated hydroxy toluene; a phenolic compound, and a monomeric or polymeric hindered amine stabilizer.

In various embodiments, the antioxidant can be a suitable free-radical scavenger, such that the antioxidant can neutralize a free-radical before the free-radical can react with oxygen to form an oxidized species. The antioxidant can be any suitable antioxidant that allows an implant including UM/AWE that can resist oxidation, such as melt-stabilized materials including UHMWPE having less or no oxidized layer when melt-stabilized in an oxygen-containing environment. The antioxidant or the multiple antioxidants can be any suitable wt. % of the liquid composition, such as about 0.01 wt. % to about 100 wt. % of the liquid composition, about 1 wt. % to about 100 wt. %, about 5 wt. % to about 100 wt. %, about 0.01 wt. % or less, or about 0.1 wt. %, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, 99.5, 99.9, 99.99, or about 99.999 wt. % of the composition or more. The one or more antioxidants can form any suitable wt. % of the material including the UHMWPE, such as the antioxidant-infused solid material including UHMWPE, the melt-consolidated material including UHMWPE, the preheated material including UHMWPE, the irradiated material including UHMWPE, or the melt-stabilized material including UHMWPE, such as about 0.01 wt. % to about 20 wt. % of the liquid composition, about 0.1 wt. % to about 5 wt. %, about 0.01 wt. % or less, or about 0.05 wt. %, 0.1, 0.2, 0.3, 0.4, 0.5, 0.6, 0.7, 0.8, 0.9, 1, 1.2, 1.4, 1.6, 1.8, 2, 2.2, 2.4, 2.6, 2.8, 3, 3.5, 4, 4.5, 5, 9, 10, 15, or about 20 wt. % or more.

In various embodiments, the antioxidant can be at least one of a tocopherol, a tocopherol phosphite (a tocopherol including a phosphite protecting group), a tocotrienol, vitamin E, vitamin E acetate, Irganox® 1010 (pentaerythritol tetrakis(3-(3,5-di-tert-butyl-4-hydroxyphenyl)propionate)), Tinuvin® 622 LD (butanedioic acid dimethyl ester/4-hydroxy-2,2,6,6-tetramethyl-1-piperidine ethanol copolymer), tannic acid, bilberry extract, vitamin C (e.g., ascorbyl palmitate or other lipid soluble forms), a carotene (e.g., vitamin A, licopene), a flavonoid (e.g., flavonol), an isoflavonoid, a neoflavonoid, a lignin (e.g., enterodiol), quinine, ubiquinone (e.g., coenzyme Q10), vitamin K1, a metal (e.g., selenium), glutathione, propyl gallate, octyl gallate, lauryl gallate, resveratrol, rosmarinic acid, rutin, 5-aminosalicylic acid, butylated hydroxy anisole (BHA), butylated hydroxy toluene (BHT), a phenolic compound (e.g., t-butyl hydroquinone), and a monomeric or polymeric hindered amine stabilizer (e.g., derivatives of 2,2,6,6-tetramethylpiperidine, such as 2,2,6,6-tetramethylpiperidin-1-yl)oxidanyl or TEMPO). In some embodiments, the antioxidant can be at least one of vitamin E, vitamin E acetate, vitamin E phosphite (vitamin E including a phosphite protecting group), pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, rosemary oil, and bilberry extract. In various embodiments, vitamin E phosphite or a tocopherol phosphite can be used, which can be deprotected to provide vitamin E or a tocopherol, respectively, using a suitable deprotection means, such as hydrolysis (e.g., exposure to water with optional acid or base).

For example, the antioxidant can be a compound of the formula (I) or (Ib):

(I)

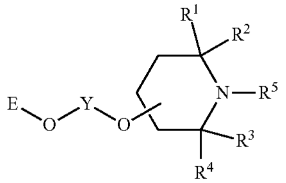

(Ib)

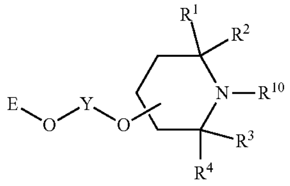

or a salt thereof or combinations thereof. The variables $R^1$, $R^2$, $R^3$, $R^4$, and $R^5$ are each, independently, hydrogen or alkyl. The variable $R^{10}$ is $-OR^{11}$ wherein $R^{11}$ is hydrogen or alkyl, or $-O^-$. The variable E represents a tocopheryl radical or a tocotrienol radical. The variable Y represents:

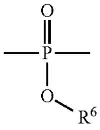

or

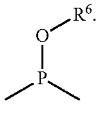

The variable $R^6$ is hydrogen, alkyl, a tocopheryl radical, a tocotrienol radical or a radical of the formula:

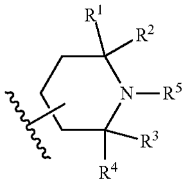

or

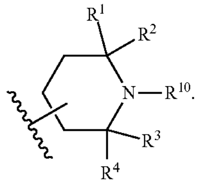

In various embodiments, the method can include deprotecting the antioxidant at any suitable stage of the method (e.g., after an irradiation step). Deprotection can occur via any suitable means, such as via hydrolysis e.g., exposure to water, as an aqueous solution or in the air).

As used herein, "vitamin E" (e.g., alone or as a derivative such as vitamin E acetate) can refer to at least one of racemic alpha-tocopherol, RRR-alpha-tocopherol, SRR-alpha-tocopherol, SSR-alpha-tocopherol, SRS-alpha-tocopherol, SSS-alpha-tocopherol, RSR-alpha-tocopherol, RRS-alpha-tocopherol, RSS-alpha-tocopherol, racemic beta-tocopherol, RRR-beta-tocopherol, SRR-beta-tocopherol, SSR-beta-tocopherol, SRS-beta-tocopherol, SSS-beta-tocopherol, RSR-beta-tocopherol, RRS-beta-tocopherol, RSS-beta-tocopherol, racemic gamma-tocopherol, RRR-gamma-tocopherol, SRR-gamma-tocopherol, SSR-gamma-tocopherol, SRS-gamma-tocopherol, SSS-gamma-tocopherol, RSR-gamma-tocopherol, RRS-gamma-tocopherol, RSS-gamma-tocopherol, racemic delta-tocopherol, RRR-delta-tocopherol, SRR-delta-tocopherol, SSR-delta-tocopherol, SRS-delta-tocopherol, SSS-delta-tocopherol, RSR-delta-tocopherol, RRS-delta-tocopherol, and RSS-delta-tocopherol.

A tocopherol can have the structure:

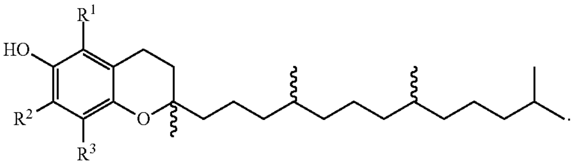

The variables $R^1$, $R^2$, and $R^3$ are each independently selected from hydrogen, substituted or unsubstituted $(C_1\text{-}C_{10})$alkyl, and substituted or unsubstituted $(C_1\text{-}C_{10})$alkenyl. The stereochemistry of the tocopherol can be racemic or at least one of RRR, SRR, SSR, SRS, RSR, RRS, RSS, and SSS. In some embodiments, $R^1$, $R^2$, and $R^3$ are each $(C_1\text{-}C_{10})$alkyl, such as methyl (e.g., alpha-tocopherol). In some embodiments, $R^1$ and $R^3$ are each $(C_1\text{-}C_{10})$alkyl, such as methyl, and $R^2$ is hydrogen (beta-tocopherol). In some embodiments, $R^2$ and $R^3$ are each $(C_1\text{-}C_{10})$alkyl, such as methyl, and $R^1$ is hydrogen (gamma-tocopherol). In some embodiments, $R^1$ and $R^2$ are each hydrogen and $R^3$ is $(C_1\text{-}C_{10})$alkyl, such as methyl (delta-tocopherol).

A tocotrienol can have the structure:

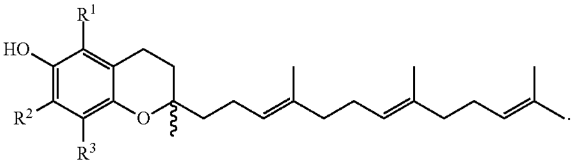

The variables $R^1$, $R^2$, and $R^3$ are each independently selected from hydrogen, substituted or unsubstituted $(C_1\text{-}C_{10})$alkyl, and substituted or unsubstituted $(C_1\text{-}C_{10})$alkenyl. The stereochemistry of the tocotrienol can be racemic or at least one of R and S. In some embodiments, $R^1$, $R^2$, and $R^3$ are each $(C_1\text{-}C_{10})$alkyl, such as methyl (e.g., alpha-tocotrienol). In some embodiments, $R^1$ and $R^3$ are each $(C_1\text{-}C_{10})$alkyl, such as methyl, and $R^2$ is hydrogen (beta-tocotrienol). In some embodiments, $R^2$ and $R^3$ are each $(C_1\text{-}C_{10})$alkyl, such as methyl, and $R^1$ is hydrogen (gamma-tocotrienol). In some embodiments, $R^1$ and $R^2$ are each hydrogen and $R^3$ is $(C_1\text{-}C_{10})$alkyl, such as methyl (delta-tocotrienol). A tocopherol or tocotrienol can be naturally occurring or synthetic.

The method of adding the antioxidant can include obtaining or providing an implant material including polyethylene. The method can include coating the implant material with a liquid composition, or alternatively incorporating. The method can include melt-consolidating the antioxidant-infused solid material, to provide a melt-consolidated material.

In certain examples, the method of adding antioxidant to polyethylene can include any suitable physical manipulation before, between, or after any suitable steps of the method (e.g., cold-sintering, coating, melt-consolidating, preheating, irradiating, or melt stabilizing), such as molding, compressing, consolidating, removing material from, or otherwise processing to provide a desired shape, part size, or other physical attributes to render the part suitable for its intended use.

In some embodiments, one or more agents, e.g., bioactive agents, can be added to the material. Such addition can be accomplished during any stage of preparation but may be desirable after any heat treatments are performed to reduce the likelihood of deactivation of the bioactive agent. Illustrative agents include an antibiotic, a steroid, a drug (e.g. analgesics), a growth factor such as bone morphogenic protein, an osteocyte, an osteoclast or other cells, a vitamin, a chondroitin, a glucosamine, a glycosoaminglycan, high energy phosphates such as phosphoenolpyruvate, ATP, 5'-AMP and other small molecule biologics or other chemical or biological agents. In some examples, the material including polyethylene can be loaded with stem cells, and the material can act as a scaffold to permit growth and differentiation of bone or cartilage within the polymer framework. The presence of an antioxidant in the material including polyethylene (e.g., via at least one of mixing with the UHMWPE powder and via coating the implant material) can act to prevent degradation of the polymer scaffold in its use environment and may also provide some oxidative protection to the bioactive agent or stem cells loaded into the scaffold.

Irradiation of Implant

The consolidated polyethylene implant can be irradiated prior to or after infusion. Irradiation can induce crosslinking irradiation in the polyethylene implant after consolidation. Alternatively or additionally, irradiation can be done to the implant after infusion. Irradiation can be done, for example, by electron beam or gamma irradiation. In general, irradiating can be done, for example, at a temperature of about 60 to about 300° C., so that crosslinking is induced. Optionally, crosslinking irradiation can be done at a temperature where the polyethylene does not melt. Irradiating can be done, for example, at a total dose of irradiation of about 1 kGy to about 100,000 kGy.

In some embodiments, the method can include preheating the melt-consolidated material prior to the crosslinking irradiation. In other embodiments, no preheating occurs prior to crosslinking irradiation (e.g., the consolidated material is approximately ambient temperature or room temperature when irradiation begins). In some embodiments, a crosslinking irradiation step can be performed shortly after consolidation, for example, such that the consolidated material has not yet completely cooled, such that the material is effectively preheated at the time of crosslinking irradiation.

In some embodiments, the preheating can include heating to a temperature above room temperature and below or above the melting point of the polyethylene or mixture of polyethylene and other components, such as about 50° C. to about 110° C., or about 50° C. or less, or about 55 or, 60, 65, 70, 75, 80, 85, 90, 95, 100, 105, 110, 115, 120, 125, 130, 140, 145, or to about 150° C., or more, such that at the time of irradiation onset the material has a preheated temperature.

The crosslinking irradiation can be any suitable irradiation. The crosslinking irradiation can be visible light radiation, infrared radiation, ultraviolet radiation, electron beam radiation, gamma radiation, or X-ray radiation. Where ionizing radiation is employed to effect the crosslinking reaction, the radiation can be obtained from any suitable source such as an atomic pile, a resonant transformer accelerator, a Van de Graaff electron accelerator, a Linac electron accelerator, a betatron, a synchrotron, a cyclotron, or the like. Radiation from these sources will produce ionizing radiation such as electrons, protons, neutrons, deuterons, gamma rays, X-rays, alpha particles, or beta particles. Where ionizing radiation is used, a sufficient radiation dose rate and/or absorbed dose can be used to induce crosslinking and/or control the degree of crosslinking. In some embodiments, during the irradiation, the temperature of the polyethylene or mixture of polyethylene and other components can be maintained below the melting point of the same.

In some embodiments, during the crosslinking irradiation, the temperature of the polyethylene or mixture of polyethylene and other components can be allowed to rise above the melting point of the same. In various embodiments, during irradiation, the temperature can be allowed to rise to, or the temperature can be maintained at, about 60° C., 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 250, 275, or about 300° C. or more.

In some embodiments, the polyethylene or mixture of polyethylene and other components can be preheated prior to irradiation, such as to a temperature above room temperature and below or above the melting point of the polyethylene or mixture of polyethylene and other components. In various embodiments, the polyethylene or mixture of polyethylene and other components can be preheated to a temperature below the melting point of the same, then subsequently irradiated while maintaining the temperature of the preheated polyethylene or mixture of polyethylene and other components below the melting point of the same.

In various embodiments, the crosslinking irradiation, such as electron-beam irradiation or gamma irradiation, uses a total dose of about 1 kGy to about 100,000 kGy, 10 kGy to about 1000 kGy, about 50 kGy to about 500 kGy, 50 kGy to 300 kGy, or about 1 kGy or less, or about 5, 10, 15, 20, 25, 50, 75, 100, 125, 150, 175, 200, 250, 300, 350, 400, 500, 750, 1,000, 1,250, 1,500, 1,750, 2,000, 2,500, 3,000, 4,000, 5,000, 7,500, 10,000, 15,000, 20,000, 25,000, 50,000, 75,000, or about 100,000 kGy or more. In various embodiments, the irradiating includes using a dose rate of about 0.001 mGy/h to about 500 MGy/h, about 1 mGy/h to about 50 MGy/h, or about 0.001 mGy/h or less, or about 0.005 mGy/h, 0.01, 0.05, 0.1, 0.5, 1, 1.5, 2, 2.5, 3, 3.5, 4, 4.5, 5, 6, 7, 8, 9, 10, 11, 12, 13, 14, 15, 16, 17, 18, 19, 20, 22, 24, 26, 28, 30, 35, 40, 45, 50, 60, 70, 80, 90, 100, 150, 200, 250, 300, 400, or about 500 MGy/h or more.

In some embodiments, crosslinking irradiating can be done, for example, in the presence of a crosslinking polymer. The crosslinking polymer can induce crosslinking within the polyethylene. The crosslinking polymer can be, for example, trimethylolpropane triacrylate, trimethylolpropane trimethacrylate, pentaerythritol tetraacrylate, pentaerythritol tetramethacrylate, or combinations thereof. Alternatively, other reagents that can scavenge free radicals can be present to reduce the degree of crosslinking.

In certain embodiments, additional components may be combined with the material including polyethylene before, between, or after any suitable steps of the method (e.g., any of consolidating, preheating, irradiating, and infusing). In one embodiment, tribological components such as metal and/or ceramic articulating components and/or preassembled bipolar components may be joined with the material including polyethylene. In other embodiments, metal backing (e.g., plates or shields) may be added. In further embodiments, surface components such a trabecular metal, fiber metal, Sulmesh™ coating, meshes, cancellous titanium, and/or metal or polymer coatings may be added to or joined with the material including polyethylene. Radio markers or radio pacifiers such as tantalum, steel and/or titanium balls, wires, bolts or pegs may be added. Locking features such as rings, bolts, pegs, snaps and/or cements/adhesives can be added. These additional components may be used to form sandwich implant designs, radiomarked implants, metal-backed implants to prevent direct bone contact, functional growth surfaces, and/or implants with locking features.

In some embodiments, the implant can additionally or alternatively be irradiated after infusion. Compared to crosslinking irradiation, this step could take place after the implant is infused with iodine and does not necessarily induce crosslinking in the implant material. In this case, irradiation can be done, for example, by electron beam or gamma irradiation. In general, irradiating can be done, for example, at a temperature of about 60° C. to about 300° C.

Infusion of Implant

The polyethylene implant can be infused with iodine (or alternatively, iodine can be mixed into the polyethylene prior to molding). In some embodiments, the polyethylene can be saturated with iodine. Free iodine is attractive to promote anti-microbial release of iodine in vivo. Povidone-iodine is a polyvinyl polymer including iodine that allows iodine to be water soluble. Povidone-iodine is a chemical complex of povidone (PVP), hydrogen iodide, and elemental iodine, having the chemical structure:

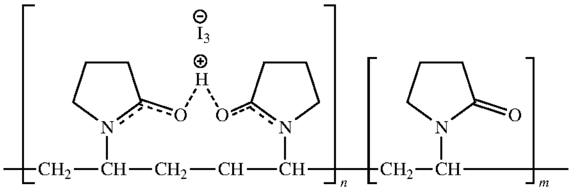

Povidone-iodine is soluble in water, ethyl alcohol, isopropyl alcohol, polyethylene glycerol, and glycerol, among other solvents. Povidone-iodine slowly releases free iodine in solution, as shown in the below equation:

$$(PVP\cdot H^{+})I_3^{-} \leftrightarrow (PVP\cdot H^{+})I^{-} + I_2$$

In solution, this equilibrium develops. The complex linked iodine is a reservoir for prolonged delivery of free iodine into solution.

Free iodine kills eukaryotic or prokaryotic cells through iodination of lipids and oxidation of cytoplasmic and membrane compounds. Specifically, free iodine can act as an anti-microbial agent to bacteria, fungi, protozoa, and viruses. Microbes do not currently have a developed resistance to free iodine.

In general, provision of anti-infective activity into a medical device or instrument (or other auxiliary materials) using iodine can be done by exposing the medical device to iodine and transferring the iodine into the polymer-based medical device. The polymer, such as, for example, the polyethylene implant material discussed herein, can be treated in either resin, powder, or consolidated form.

In some embodiments, the povidone-iodine can be mixed directly into the powdered polyethylene material prior to molding. However, blending of iodine into a resin or powder of the polyethylene may affect consolidation of the resin.

Thus, infusion of iodine to an implant material in a consolidated form (e.g., consolidated sheet, bar, extruded, or net) is preferred.

The minimum concentration of iodine required to achieve antimicrobial activity is about 2 ppm povidone-iodine. Thus, the concentration of a povidone-iodine solution used to infuse a polyethylene implant herein can be, for example, above 0.002 mg/mL.

In some embodiments, the source of iodine can be a solution containing iodine, such as a povidone-iodine solution, making iodine water-soluble. With a povidone-iodine solution, the concentration can be, for example, about 0.1 wt. % to about 10.0 wt. % povidone-iodine about 1.0 wt. % to about 3.0 wt. % povidone-iodine).

Where the iodine source is an iodine solution, the iodine can be in a solvent that is, for example, a protic solvent, such as water, ethanol, isopropanol, or other appropriate solvents. When using water as a solvent, the iodine can be, for example, from 0.1% to 10% W/W. A polar solvent is used to create the desired concentration of the oxidizing agent (e.g., water, ethyl alcohol, isopropyl alcohol, polyethylene glycerol, glycerol). Alternatively, a different complex containing iodine ($I_2$) or iodide ($I^-$) can be used.

The ratio by weight of the iodine-containing agent, povidone-iodine (or other appropriate iodine containing oxidizing agent) to the polyethylene can be, for example, about 1:1 to above 50:1 povidone-iodine solution to polyethylene. A ratio of above zero can be used. A ratio of 50:1 or above is effective, with a fast rate of infusion. A large ratio can provide a reservoir of iodine.

Infusion of the polyethylene implant can be done, for example, by immersion or submersion of the polyethylene implant in the iodine solution after consolidation of the implant. For example, the polyethylene implant can be placed in a bath of the iodine solution.

In some examples, the bath can be warmed to allow efficient uptake of iodine into the polyethylene. The bath can be warmed, for example, from about room temperature e.g. about 25° C.) to about 100° C. about 80° C. to about 95° C.). Heating can be done during infusion of the polyethylene. The bath can be warmed so that the iodine infuses at a quicker rate, but not so warm as to effect the integrity of the consolidated polyethylene. Temperatures above 100° C. can potentially damage mechanical properties of the polyethylene, affecting long term use of implants. In some embodiments, the iodine-infused polyethylene can also be post-heated to increase homogeneity and depth of the povidone-iodine.

The immersion can be done, for example, for about 1 hour to about 16 days, or alternatively for up to about 30 days, or until the consolidated polyethylene is saturated.

A whole polyethylene implant form may be infused with iodine, or only certain features may be infused with iodine, e.g. the rim of an acetabular cup. Particular portions of the implant can be, for example, masked or not immersed during infusion. The concentration of iodine may also be varied across the form through masking or selective exposure of the form.

The infusion of iodine into UHMWPE or other polymers containing an antioxidant, such as Vitamin E, can reduce any oxidation of the material due to the oxidative activity of the iodine.

EXAMPLES

Various embodiments of the present invention can be better understood by reference to the following Examples which are offered by way of illustration. The present invention is not limited to the Examples given herein.

Example 1

Preparation of Iodine-Infused Polyethylene Samples

Iodine-infused polyethylene samples were prepared using the materials summarized in Table 1 below.

TABLE 1

Iodine-infused Polyethylene Samples.

| | Iodine Source | Iodine Concentration | Infusion Conditions | Polyethylene | Antioxidant | Radiation Dose |
|---|---|---|---|---|---|---|
| Sample A | Povidone-iodine | 10% W/W povidone-iodine in DI water | 14 days 60° C. | UHMWPE | None | 25-40 kGy post iodine infusion |
| Sample B | Povidone-iodine | 10% W/W povidone-iodine in DI water | 14 days 60° C. | UHMWPE | Vitamin E | 25-40 kGy Post Vitamin E & iodine infusion |
| Sample C | Povidone-iodine | 10% W/W povidone-iodine in DI water | 14 days 60° C. | HXLPE | Vitamin E | Total 100 kGy (crosslinking and sterilization). Crosslinking post Vitamin E & prior to iodine infusion & final sterilization dose post iodine infusion |

The iodine solution used was a povidone-iodine #10730575 from Organics (Geel, Belgium). The various polyethylene used included an ultra-high molecular weight polyethylene (UHMWPE), a Vitamin E UHMWPE, and a vitamin F highly crosslinked polyethylene.

First, the polyethylene was formed into the implant shape and consolidated. The polyethylene powder was cold sintered in a 2 inch diameter cylindrical compression mold under 21 tons of force for 30 minutes at ambient temperature.

In samples B & C, a 17 wt. % solution of vitamin E dissolved in isopropyl alcohol was applied uniformly to the exterior of the cold sintered cylindrical form with a cotton swab. The total vitamin E applied was approximately four to five grams. The cold sintered form readily absorbed the entire solution applied. The form was allowed to dry for 12 hours at ambient temperature, under nitrogen purge. In all samples, the form was then inserted back into the compression mold and was consolidated under pressure above the melting point of the polyethylene.

Subsequently, Sample C was treated with crosslinking irradiation. For Samples A, B and C, gamma irradiation was used at a dose of from about 25 kGy to about 45 kGy (for sterilization) and a temperature of about 60° C. to about 300° C.

After consolidation and optional crosslinking irradiation (of Sample C), the samples were infused with povidone-iodine. The povidone-iodine solution was prepared in deionized (DI) water at 10% W/W (weight ratio) using about 10 g povidone-iodine for each 90 g DI. Three 150 mL baths of the 10% povidone-iodine solution. The three polyethylene samples A, B, and C were each submerged in a bath. Each bath container was placed in a hot water bath at an average temperature of about 60° C. Temperature of about 60° C. allowed for intake of iodine at a reasonable rate without degradation of the consolidated polyethylene. The samples were submerged for 14 days. The resulting samples slowly changed in color as iodine was infused in the polyethylene samples.

The UHMWPE+Iodine samples A-C were tested for iodine concentration on two locations of the polyethylene implant after infusion, sterilization, and aging. The samples were tested with x-ray fluorescence (XRF) using a 10 mm diameter aperture. The analysis of the sample showed the following density of povidone-iodine:

TABLE 2

Amount of povidone-iodine in sample.

| | Density (μg/$cm^3$) |
|---|---|
| Location 1 | 71.161 |
| Location 2 | 62.276 |

The XRF measurements analyzed the density of povidone-iodine in the sample. The sample showed from about 70 to about 90 μg/$cm^3$ povidone-iodine depending on the location tested.

Example 2

Elution from Iodine-Infused Polyethylene Samples

The samples from Example 1 were maintained at 50° C. and tested for release of iodine over time. The release study was carried out in exaggerated conditions compared to a human body. The samples were placed in water baths of about 50° C. The sample conditions are summarized below in Table 3:

TABLE 3

Aged Iodine-infused Polyethylene Samples

| | Starting Sample | Polyethylene | Antioxidant | Elution Conditions |
|---|---|---|---|---|
| Sample D | A | UHMWPE | None | Water Bath 50° C., 21 days |
| Sample E | B | UHMWPE | Vitamin E | Water Bath 50° C., 21 days |
| Sample F | C | HXPE | Vitamin E | Water Bath 50° C., 21 days |
| Control | | Virgin UHMWPE | None | Water Bath 50° C., 21 days |

All samples D-F were gamma sterilized at about 25 kGy to about 27 kGy prior to aging. The release of iodine was observed over a 21 day period. The coloring of the samples D (iodine-infused F (vitamin E containing iodine-infused UHMWPE), and the control UHMWPE was observed over period of 1, 14, and 21 days. The majority of iodine was released after about 21 days in these conditions. It is expected that iodine will take much longer to release in physiological conditions.

Example 3

Oxidation Index of Iodine-Infused Polyethylene Samples

Samples were also tested for oxidative degradation, wear analysis, and mechanical properties. Samples were aged using elevated temperature and elevated oxygen pressure in accordance with ASTM F2003-02 (2015), The aged samples were compared to UHMWPE (as obtained), aged UHMWPE, and other aged polymer samples. The samples tested are summarized in Table 4 below.

TABLE 4

Samples Tested for Oxidation Index in Example 3.

| | Description | Conditions |
|---|---|---|
| "UHMWPE" | UHMWPE | 2,5-40 kGy sterilization dose and aging. |
| "Iodine UHMWPE" | UHMWPE infused with Iodine | Iodine infusion, 25-40 kGy sterilization dose and aging. |
| "VE UHMWPE" | Vitamin E-blended UHMWPE | Blended with Vitamin E prior to consolidation. 25-40 kGy sterilization dose and aging. |
| "VE Iodine UHMWPE" | Vitamin E-blended UHMWPE infused with iodine | Vitamin E blended prior to consolidation. Iodine infusion after consolidation & prior to final sterilization (25-40 kGy dose) and aging. |
| "HXLPE VE" | Vitamin E-blended HXLPE | Total 100 kGy (crosslinking and sterilization). Vitamin E-blended prior to consolidation, crosslinking, final sterilization and aging. |
| "HXLPE VE Iodine" | Vitamin E-blended HXLPE infused with iodine | Total 100 kGy (crosslinking and sterilization). Vitamin E-blended prior to consolidation and crosslinking. Infusion with iodine prior to final sterilization and aging. |

FIG. 1 depicts the oxidation index of each sample (UHMWPE, Iodine UHMWPE, VE UHMWPE, VE Iodine UHMWPE, HXLPE VE, and HXLPE VE Iodine), described in more detail in Table 4 above. The oxidation index of the samples treated with iodine were generally low, with the exception of the "Iodine UHMWPE" sample without Vitamin E.

The samples infused with Vitamin E, an antioxidant, had oxidation indexes lower than 1. Overall, there was no oxidation e.g., an oxidation index below 1 in the graph) for all Vitamin E infused polymers. There is oxidation only in the case of the iodine-infused UHMWPE (e.g., an oxidation index above 1).

Example 4

Mechanical Properties of Iodine-Infused Polyethylene Samples

Figure 2:
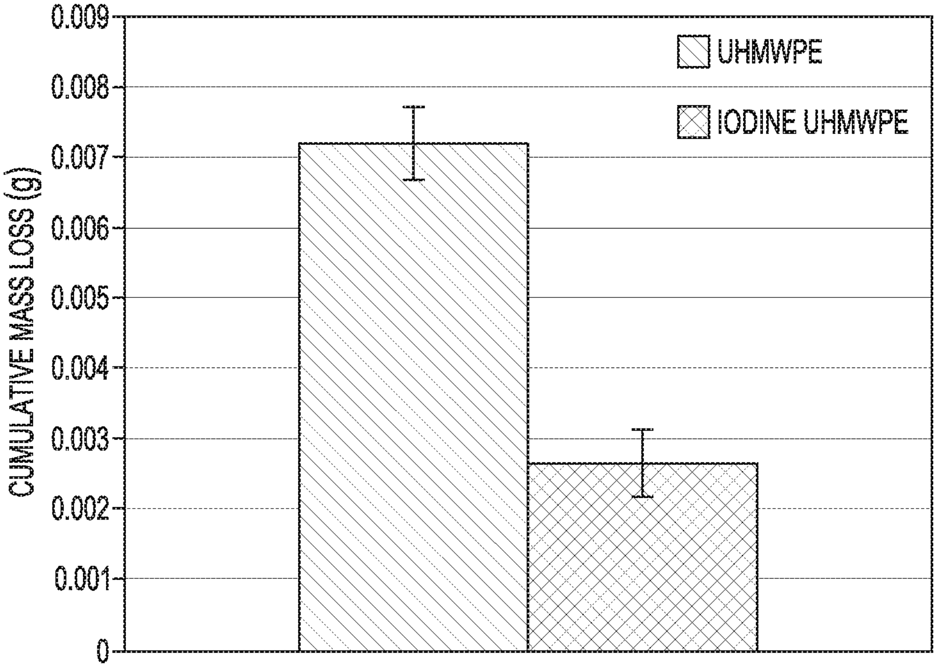
FIG. 2 is a graph depicting wear properties of samples in Example 4, in accordance with various embodiments.

Iodine-infused polyethylene samples were also tested for wear analysis using a pin-on-plate analysis, shown in FIG. 2. The weight of the samples was measured to show the mean cumulative mass loss per cycles of pin-on-plate wear analysis. Shown in FIG. 2, a sample of UHMWPE infused with iodine, but not aged is compared to virgin UHMWPE. Here, the virgin UHMWPE showed up to 0.0072 g mean cumulative mass loss by 1,000,000 cycles of testing, compared to the iodine-infused sample with about 0.0028 g mean cumulative mass loss by 1,000,000 cycles of testing.

Figure 3A:
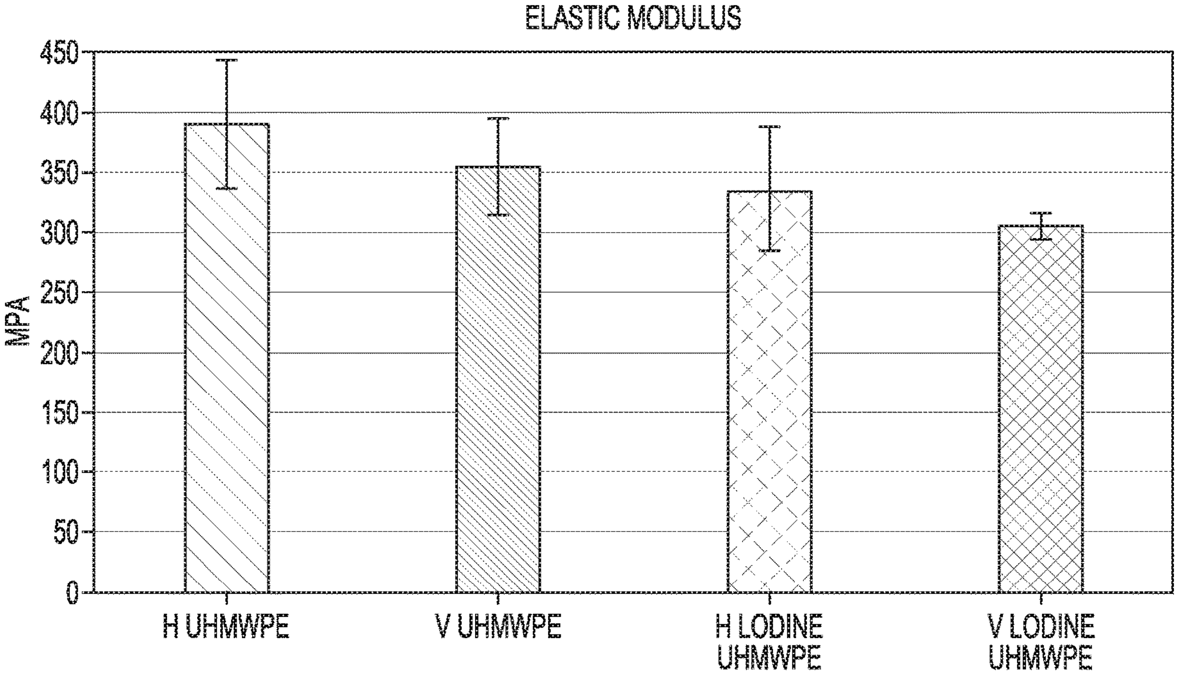
FIGS. 3A-3D are graphs depicting mechanical properties of samples in Example 4, in accordance with various embodiments.
Figure 3B:
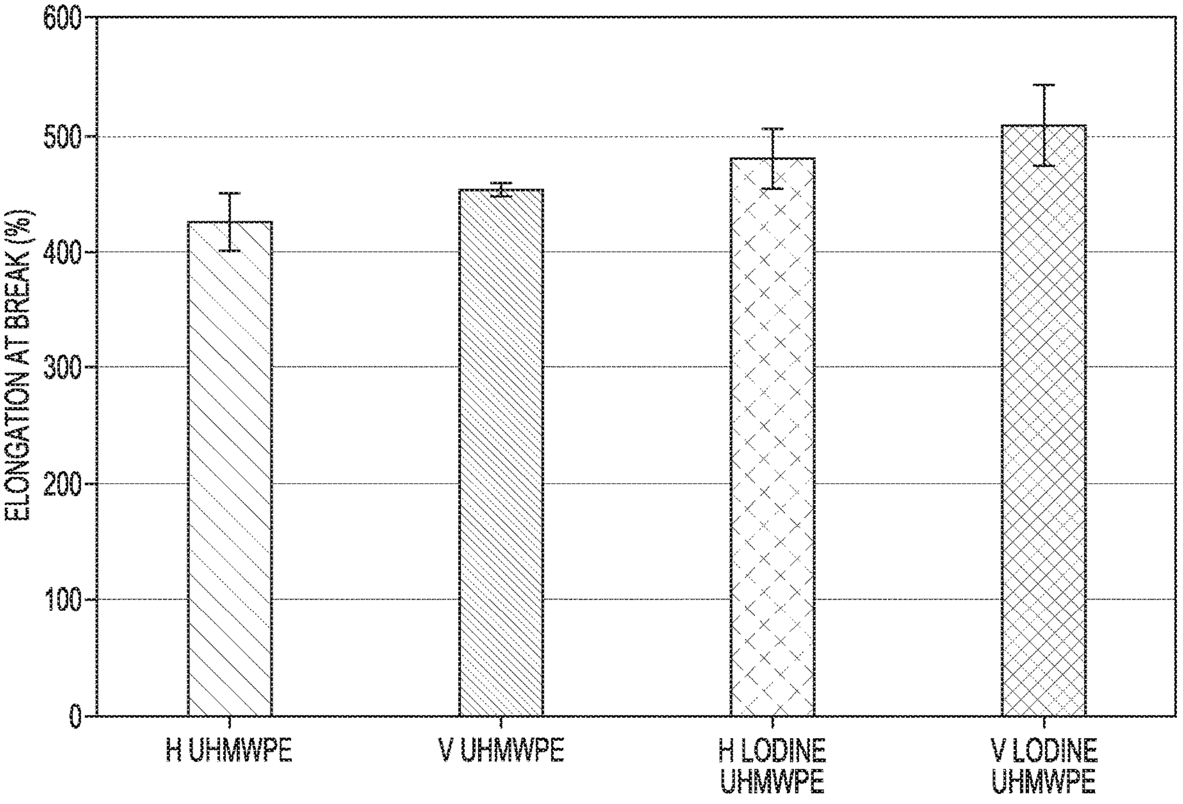
Figure 3C:
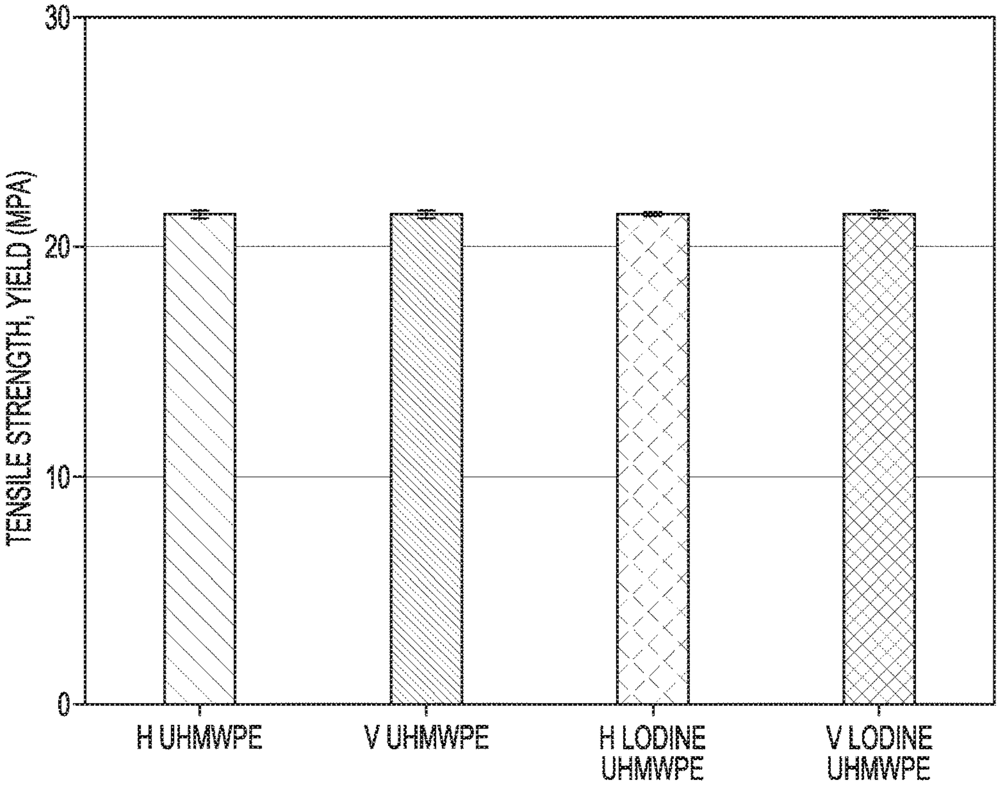
Figure 3D:
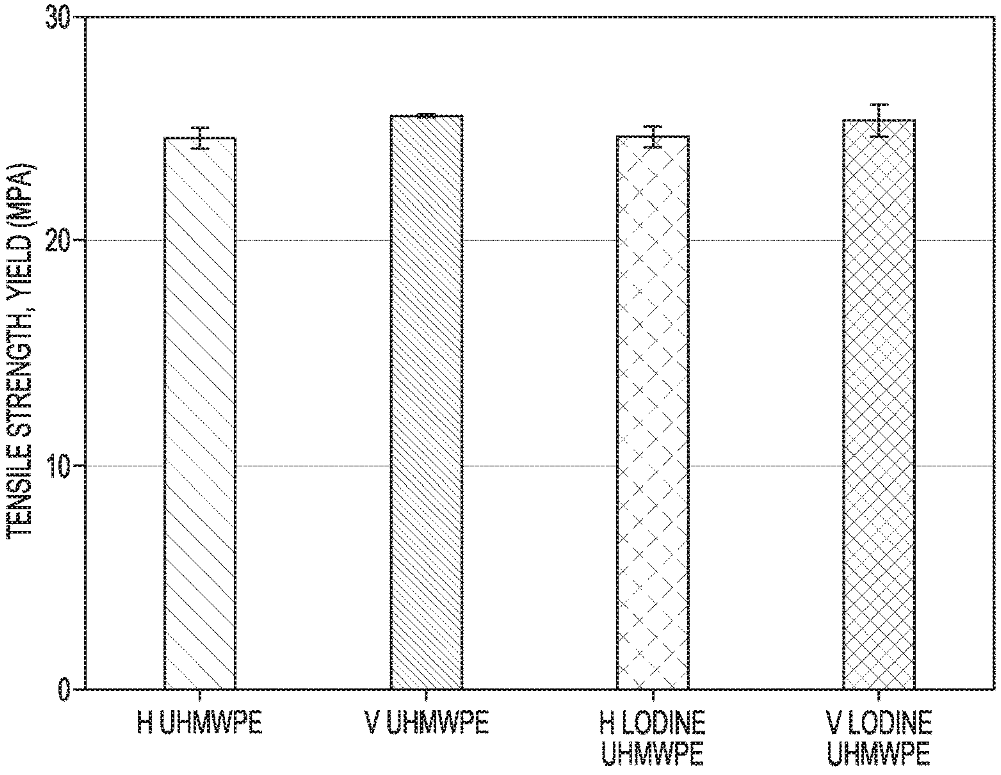

The samples were additionally tested for mechanical properties, including elastic modulus and extension at break, shown in FIGS. 3A, 3B, respectively. Samples tested for mechanical properties included UHMWPE ("H UHMWPE" and "V UHMWPE") in addition to iodine-infused UHMWPE ("H Iodine UHMWPE" and "V Iodine UHMWPE"). The samples included both those machined with flat face normal to the direction of molding ("H") and samples of thin sections normal to the direction of molding ("V"). The mechanical properties were tested with an Instron 5985 calibrated with a 50 kN load cell. The testing procedure used was a standard ASTM D638-10 procedure at a rate of 5.0 mm/min.

As shown in FIGS. 3A-3D, the samples showed an elastic modulus of about 300 MPa to about 350 MPa for the iodine-infused UHMWPE, compared to an elastic modulus of about 350 MPa to about 400 MPs for the non-infused UHMWPE. The samples showed an elongation at break of about 475% to about 515% for the iodine-infused UHMWPE, compared to an elongation at break of about 415% to about 450% for the non-infused UHMWPE.

Tensile strength at yield of both the iodine infused samples and the virgin samples was about 20 MPa to about 22 MPa. However, tensile strength at break was about 25 MPa to about 27 MPa for the iodine infused samples compared to about 24 MPa to about 25 MPa. Overall, as the samples were tested for mechanical properties, they became more ductile. In general, the addition of iodine to the UHMWPE did not affect the mechanical properties of the samples.

Figure 4:
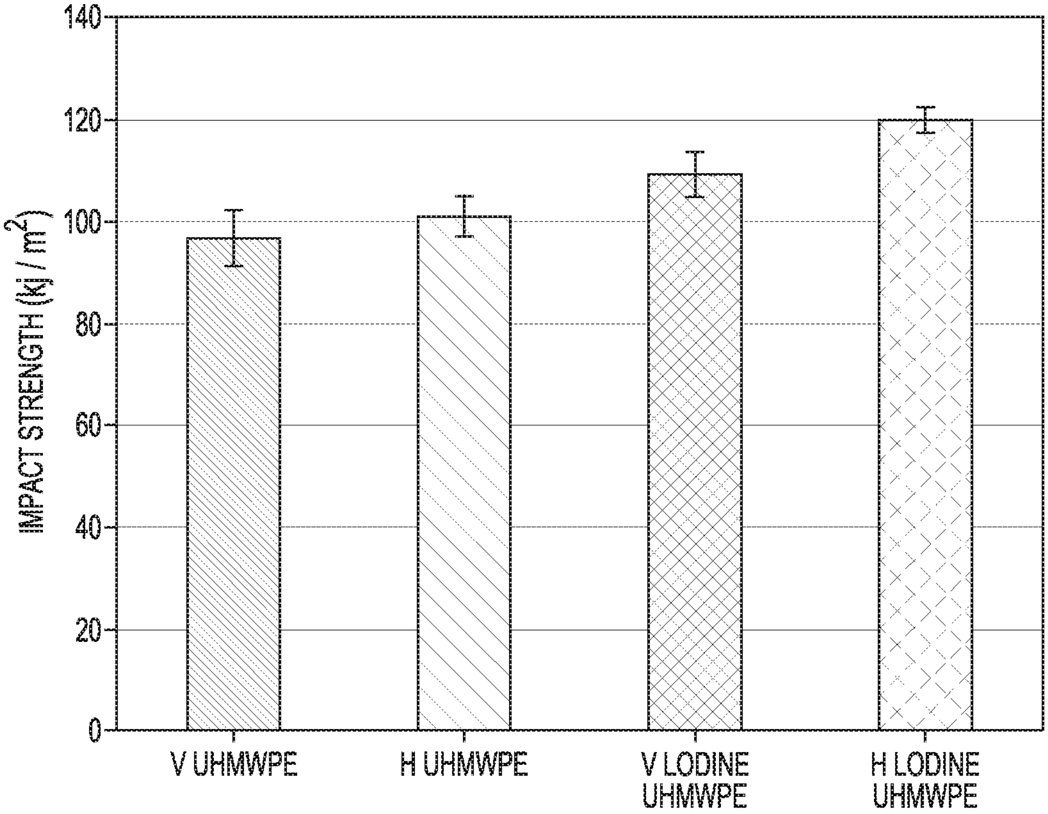
FIG. 4 is a graph depicting the impact strength of samples in Example 4.
Figure 5:
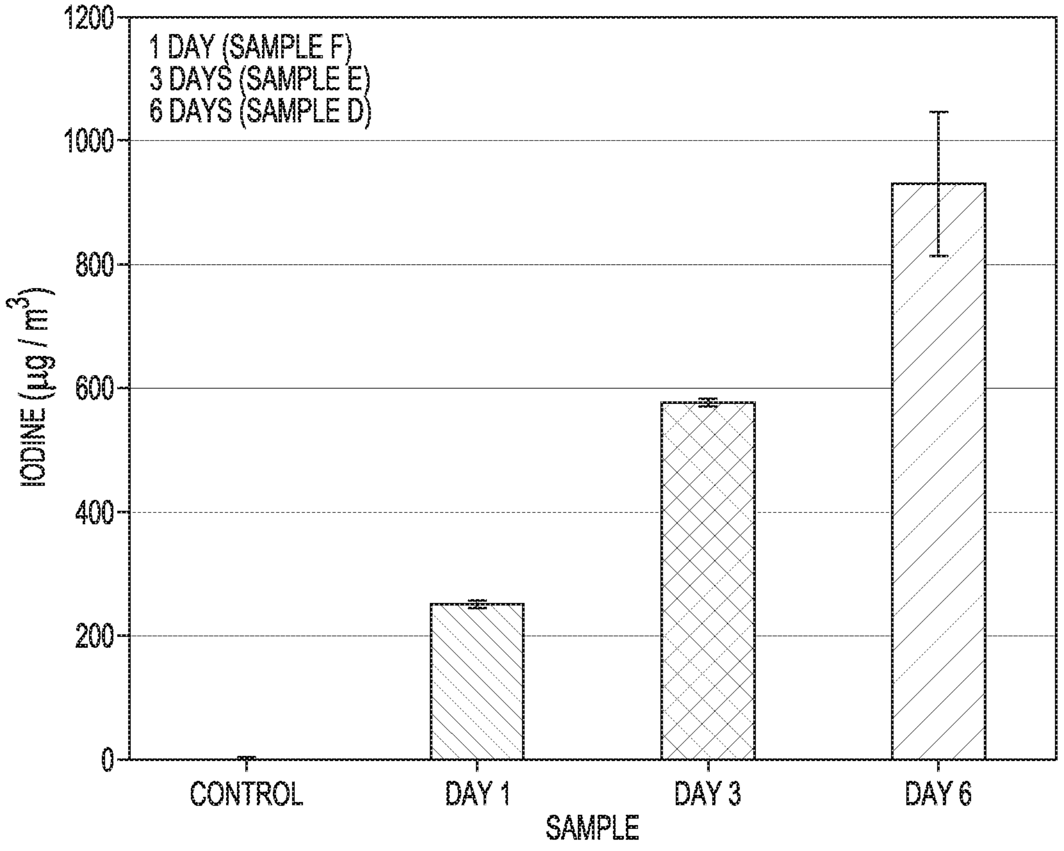
FIG. 5 is a graph depicting iodine amounts in samples in Example 5.

FIG. 4 depicts impact strength (in $kJ/m^2$) of the samples. Here, the virgin UHMWPE sample had an average impact strength of about 100 $kJ/m^2$, while the iodine-infused UHMWPE samples had an average higher impact strength of about 120 $kJ/m^2$.

Example 5

A second set of iodine-infused polyethylene samples were prepared using the materials summarized in Table 5 below.

TABLE 5

Iodine-infused Polyethylene Samples.

| | Iodine Source | Iodine Concentration | Infusion Conditions | Polyethylene | Antioxidant | Radiation Dose |
|---|---|---|---|---|---|---|
| Sample G | Povidone-iodine | 1% W/W povidone-iodine in DI water | 6 days 95° C. | UHMWPE | None | None |
| Sample H | Povidone-iodine | 1% W/W povidone-iodine in DI water | 3 days 95° C. | UHMWPE | None | None |
| Sample I | Povidone-iodine | 1% W/W povidone-iodine in DI water | 1 day 95° C. | UHMWPE | None | None |
| Sample J | Povidone-iodine | 1% W/W povidone-iodine in DI water | 5 days 95° C. | UHMWPE | None | None |
| Sample K | Povidone-iodine | 2% W/W povidone-iodine in DI water | 5 days 95° C. | UHMWPE | None | None |
| Sample L | Povidone-iodine | 3% W/W povidone-iodine in DI water | 5 days 95° C. | UHMWPE | None | None |
| Sample M | Povidone-iodine | 2% W/W povidone-iodine in DI water | 3 days 95° C. | UHMWPE | None | None |
| Sample N | Povidone-iodine | 3% W/W povidone-iodine in DI water | 3 days 95° C. | UHMWPE | None | None |
| Sample O | Povidone-iodine | 2% W/W povidone-iodine in DI water | 1 day 95° C. | UHMWPE | None | None |
| Sample P | Povidone-iodine | 3% W/W povidone-iodine in DI water | 1 day 95° C. | UHMWPE | None | None |
| Sample Q | Lugol's solution | 10 wt % KI and 5 wt % $I_2$ in water | 5 days 95° C. | UHMWPE | None | None |
| Sample R | Lugol's solution | 10 wt % KI and 5 wt % $I_2$ in water | 3 days 95° C. | UHMWPE | None | None |
| Sample S | Lugol's solution | 10 wt % KI and 5 wt % $I_2$ in water | 1 day 95° C. | UHMWPE | None | None |

The povidone-iodine used was Polyvinylpyrrolidone-iodine complex from Acres Organics (Creel, Belgium). The Lugol's solution used was Lugol's iodine 15% from APC Pure (Chesire, United Kingdom). The various polyethylenes used included an ultra-high molecular weight polyethylene (UHMWPE).

First, the polyethylene was formed into the implant shape and consolidated. The polyethylene powder was cold sintered in a 2 inch diameter cylindrical compression mold under 21 tons of force for 30 minutes at ambient temperature.

After consolidation, the samples were infused with iodine in a povidone-iodine solution or Lugol's solution. The povidone-iodine solution was prepared in deionized (DI) water at 0.1 to 10% W/W (weight ratio). The Lugol's solution was used as received. The polyethylene samples were each submerged in a bath of between about 150 mL to about 1 L of the respective solution. Each bath container was placed in a hot water bath at an average temperature of about 60° C. and up to about 95° C. The temperatures used allowed for intake of iodine at a reasonable rate without degradation of the consolidated polyethylene. The samples were submerged for 1 to 14 days. The resulting samples changed in color as iodine was infused in the polyethylene samples.

The iodine-infused UHMWPE samples were tested for iodine concentration on different locations after infusion. The samples were tested with x-ray fluorescence (XRF) using a 3 mm diameter aperture. For example, analysis of the UHMWPE samples D-F infused in 1% W/W showed the following iodine concentration over 6 days:

TABLE 2

Amount of povidone-iodine in sample.

| | Iodine concentration (μg/$cm^3$) |
|---|---|
| Sample G (6 days in 1% W/W PVP-I) | 929.1 |
| Sample H (3 days in 1% W/W PVP-I) | 575.6 |
| Sample I (1 day in 1% W/W PVP-I) | 253.5 |

The XRF measurements measured the concentration of iodine in the sample. The sample showed from about 250 to about 930 μg/$cm^3$ iodine depending on the infusion time.

ADDITIONAL EMBODIMENTS

The following example embodiments are provided, the numbering of which is not to be construed as designating levels of importance:

Embodiment 1 includes an implant comprising a cross-linked iodine-infused polyethylene.

Embodiment 2 includes Embodiment 1, wherein the iodine has an average concentration in the polyethylene implant of about 5 to about 3000 μg/$cm^3$.

Embodiment 3 includes any of Embodiments 1-2, wherein the iodine has an average concentration in the polyethylene implant of about 200 to about 1000 μg/$cm^3$.

Embodiment 4 includes any of Embodiments 1-3, wherein the iodine is homogeneously distributed in the polyethylene.

Embodiment 5 includes any of Embodiments 1-4, wherein the polyethylene is saturated with the iodine.

Embodiment 6 includes any of Embodiments 1-5, wherein the polyethylene comprises ultra high molecular weight polyethylene, ultra low molecular weight polyethylene, high density polyethylene, high molecular weight polyethylene, high density crosslinked polyethylene, medium density polyethylene, low density polyethylene, linear low density polyethylene, very low density polyethylene, branched polyethylene, or combinations thereof.

Embodiment 7 includes any of Embodiments 1-6, wherein the polyethylene comprises an antioxidant.

Embodiment 8 includes any of Embodiments 1-7, wherein the antioxidant comprises at least one of a tocopherol, a tocopherol phosphite, a tocotrienol, vitamin E, vitamin E acetate, vitamin E phosphite, rosemary oil, pentaerythritol tetrakis(3-(3,5-di-tert-butyl-4-hydroxyphenyl) propionate), butanedioic acid dimethyl ester/4-hydroxy-2,2,6,6-tetramethyl-1-piperidine ethanol copolymer, tannic acid, bilberry extract, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol, rosmarinic acid, rutin, 5-aminosalicylic acid, butylated hydroxy anisole, butylated hydroxy toluene, a phenolic compound, and a monomeric or polymeric hindered amine stabilizer.

Embodiment 9 includes any of Embodiments wherein the antioxidant is homogenously distributed in the polyethylene.

Embodiment 10 includes any of Embodiments 1-9, wherein the antioxidant is from about 0.01 wt. % to about 5.0 wt. % of the polyethylene.

Embodiment 11 includes any of Embodiments 1-10, wherein the antioxidant is from about 0.05 wt. % to about 0.50 wt. % of the polyethylene.

Embodiment 12 includes any of Embodiments 1-11, wherein the implant is a hip, knee, shoulder, back, elbow, chest, pectus, foot, ankle, or dental implant.

Embodiment 13 includes any of Embodiments 1-12, wherein the polyethylene has a mean cumulative mass loss from about 0.001 g to about 0.005 g over about 10,000 cycles to about 1,300,000 cycles of wear analysis in a pin-on-plate analysis.

Embodiment 14 includes any of Embodiments 1-13, wherein the polyethylene has a mean cumulative mass loss from about 0.001 g to about 0.003 g over about 20,000 cycles to about 1,200,000 cycles of wear analysis in a pin-on-plate analysis.

Embodiment 15 includes any of Embodiments 1-14, wherein the polyethylene has an elastic modulus of about 250 MPa to about 400 MPa.

Embodiment 16 includes any of Embodiments 1-15, wherein the polyethylene has an elastic modulus of about 300 MPa to about 350 MPa.

Embodiment 17 includes any of Embodiments 1-16, wherein the polyethylene has an elongation at break of about 475% to about 515%.

Embodiment 18 includes any of Embodiments 1-17, wherein the polyethylene has an elongation at break of about 490% to about 505%.

Embodiment 19 includes any of Embodiments 1-18, wherein the polyethylene has an oxidation index of about 0 to about 8.

Embodiment 20 includes any of Embodiments 1-19, wherein the polyethylene has an oxidation index of about 0 to about 1.

Embodiment 21 includes a method of making an implant comprising polyethylene, the method comprising: exposing the polyethylene to a source of iodine such that the polyethylene is infused with iodine.

Embodiment 22 includes Embodiment 21, wherein the polyethylene infused with iodine is saturated with iodine.

Embodiment 23 includes any of Embodiments 21-22, wherein the sour of ce iodine comprises a solution comprising the iodine.

Embodiment 24 includes any of Embodiments 21-23, wherein the source of iodine comprises an iodophor selected from the group consisting of povidone-iodine and aqueous iodine solutions.

Embodiment 25 includes any of Embodiments 21-24, wherein the solution comprising the iodine comprises a solvent that is a protic solvent.

Embodiment 26 includes any of Embodiments 21-25, wherein the protic solvent is water, ethanol, or isopropanol.

Embodiment 27 includes any of Embodiments 21-26, wherein the implant further comprises an antioxidant.

Embodiment 28 includes any of Embodiments 21-27, further comprising adding the antioxidant to the implant.

Embodiment 29 includes any of Embodiments 21-28, wherein adding the antioxidant comprises blending or infusion.

Embodiment 30 includes any of Embodiments 21-29, wherein the solution comprising the iodine is about 0.1 wt. % to about 10.0 wt. % povidone-iodine.

Embodiment 31 includes any of Embodiments 21-30, wherein the solution comprising the iodine is about 1.0 wt. % to about 3.0 wt. % povidone-iodine.

Embodiment 32 includes any of Embodiments 21-31, wherein infusing comprises immersing the polyethylene in the iodine solution.

Embodiment 33 includes any of Embodiments 21-3 wherein immersing the polyethylene is done for up to about 30 days.

Embodiment 34 includes any of Embodiments 21-33, wherein immersing the polyethylene is done for about 1 hour to about 16 days.

Embodiment 35 includes any of Embodiments 21-34, wherein immersing the polyethylene is done at about 20 to about 100 degrees Celsius.

Embodiment 36 includes any of Embodiments 21-35, wherein immersing the polyethylene is done at about 60 to about 95 degrees Celsius.

Embodiment 37 includes any of Embodiments 21-36, wherein a ratio by weight of the solution comprising the iodine to the polyethylene is about 1:1 to about 50:1.

Embodiment 38 includes any of Embodiments 21-37, further comprising consolidating the polyethylene prior to infusing.

Embodiment 39 includes any of Embodiments 21-38, further comprising irradiating the polyethylene after infusing.

Embodiment 40 includes any of Embodiments 21-39, wherein irradiating comprises at least one of electron beam irradiating and gamma irradiating.

Embodiment 41 includes any of Embodiments 21-40, wherein the irradiating is done at a temperature of about 60° C. to about 300° C.

Embodiment 42 includes any of Embodiments 21-41, wherein the irradiating comprises a total dose of irradiation of about 1 kGy to about 100,000 kGy.

Embodiment 43 includes any of Embodiments 21-42, further comprising preheating the polyethylene prior to irradiating.

Embodiment 44 includes any of Embodiments 21-43, wherein the irradiating induces crosslinking the polyethylene.

Embodiment 45 includes any of Embodiments 21-44, wherein the irradiating is done in the presence of a crosslinking polymer.

Embodiment 46 includes any of Embodiments 21-45, wherein the crosslinking polymer is at least one of trimethylolpropane triacrylate, trimethylolpropane trimethacrylate, pentaerythritol tetraacrylate, pentaerythritol tetramethacrylate, and combinations thereof.

Embodiment 47 includes a method of preventing microbe formation on or around an implant comprising: implanting a crosslinked iodine-infused implant comprising polyethylene, wherein iodine is released gradually from the implant after the implantation.

Embodiment 48 includes Embodiment 47, wherein releasing iodine gradually comprises releasing iodine over a period of about 15 days to about ten years.

Embodiment 49 includes any of Embodiments 47-48, wherein releasing iodine gradually comprises releasing iodine over a period of about 15 days to about 30 days.

Embodiment 50 includes any of Embodiments 47-49, wherein the method substantially prevents bacteria growth on a surface of the implant.

Embodiment 51 includes any of Embodiments 47-50, wherein the method substantially prevents biofilm formation on a surface of the implant.

What is claimed is:

1. An implant comprising:

a consolidated, anti-microbial material, formed of ultra high molecular weight polyethylene (UHMWPE) infused with iodine, an average concentration of the iodine in the anti-microbial material being within a range of 5 to 3000 micrograms per cubic centimeter (μg/$cm^3$), wherein the UHMWPE comprises crosslinking formed by an irradiation treatment;

wherein the infused iodine of the consolidated, anti-microbial material is water-soluble, such that when the material is placed in an aqueous environment, the material releases at least some of the infused iodine into the aqueous environment; and wherein the infused iodine is held in amorphous regions of the anti-microbial material.

2. The implant of claim 1, wherein the iodine compound has an average concentration in the anti-microbial material within a range of 200 to 1000 μg/$cm^3$.

3. The implant of claim 1, wherein the UHMWPE comprises a fat-soluble antioxidant additive or coating comprising at least one of a tocopherol, a tocopherol phosphite, a tocotrienol, vitamin E, vitamin E acetate, vitamin E phosphite, rosemary oil, pentaerythritol tetrakis(3-(3,5-di-tert-butyl-4-hydroxyphenyl) propionate), butanedioic acid dimethyl ester/4-hydroxy-2,2,6,6-tetramethyl-1-piperidine ethanol copolymer, tannic acid, bilberry extract, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol, rosmarinic acid, rutin, 5-aminosalicylic acid, butylated hydroxy anisole, butylated hydroxy toluene, a phenolic compound, and a monomeric or polymeric hindered amine stabilizer.

4. The implant of claim 3, wherein the antioxidant is from about 0.01 wt. % to about 5.0 wt. % of the UHMWPE.

5. The implant of claim 1, wherein the anti-microbial material has a mean cumulative mass loss from about 0.001 g to about 0.005 g over about 10,000 cycles to about 1,300,000 cycles of wear analysis in a pin-on-plate analysis.

6. The implant of claim 1, wherein the anti-microbial material has an elastic modulus of about 250 MPa to about 400 MPa.

7. The implant of claim 1, wherein the anti-microbial material has an elongation at break of about 475% to about 515%.

* * * * *